United States Patent [19]

Willms et al.

[11] Patent Number: 5,571,772
[45] Date of Patent: Nov. 5, 1996

[54] MIXTURES OF TRIAZINE SULFONYLUREA HERBICIDES AND PYRAZOLINE SAFENERS

[75] Inventors: Lothar Willms, Hofheim; Hermann Bieringer, Eppstein; Erwin Hacker, Hochheim; Heinz Kehne, Hofheim, all of Germany

[73] Assignee: Hoechst Schering AgrEvo GmbH, Germany

[21] Appl. No.: 314,326

[22] Filed: Sep. 28, 1994

[30] Foreign Application Priority Data

Sep. 30, 1993 [DE] Germany ............... 43 33 249.8

[51] Int. Cl.$^6$ .............. A01N 43/56; A01N 43/66
[52] U.S. Cl. ............................................. 504/106
[58] Field of Search ............................... 504/106

[56] References Cited

U.S. PATENT DOCUMENTS

| | | | |
|---|---|---|---|
| 4,383,113 | 5/1983 | Levitt | 544/211 |
| 4,566,898 | 1/1986 | Reap | 71/93 |
| 4,645,527 | 2/1987 | Amuti et al. | 504/111 |
| 4,881,966 | 11/1989 | Nyffeler et al. | 546/177 |
| 4,891,057 | 1/1990 | Sohn et al. | 548/377 |
| 4,902,340 | 2/1990 | Hubele | 546/178 |
| 5,104,441 | 4/1992 | Hamprecht et al. | 544/321 |
| 5,314,863 | 5/1994 | Loher et al. | 504/100 |
| 5,371,060 | 12/1994 | Glock et al. | 504/106 |

FOREIGN PATENT DOCUMENTS

| | | |
|---|---|---|
| 49026/85 | 10/1984 | Australia . |
| 34951/89 | 11/1989 | Australia . |
| 89897/91 | 12/1990 | Australia . |
| 14851/92 | 4/1991 | Australia . |
| 44286/93 | 8/1992 | Australia . |
| 2058276 | 6/1992 | Canada . |
| 2101684 | 2/1994 | Canada . |
| 0007687 | 2/1980 | European Pat. Off. . |
| 0127469 | 12/1984 | European Pat. Off. . |
| 0182740 | 5/1986 | European Pat. Off. . |
| 0269806 | 6/1988 | European Pat. Off. . |
| 0291851 | 11/1988 | European Pat. Off. . |
| 0333137 | 9/1989 | European Pat. Off. . |
| 0346620 | 12/1989 | European Pat. Off. . |
| 0492367 | 7/1992 | European Pat. Off. . |
| 0492366 | 7/1992 | European Pat. Off. . |
| 0509433A1 | 10/1992 | European Pat. Off. . |
| 0558448 | 9/1993 | European Pat. Off. . |
| 0582198 | 2/1994 | European Pat. Off. . |
| 3900472 | 7/1990 | Germany . |
| 89/1960 | 3/1989 | South Africa . |
| 90/9591 | 11/1990 | South Africa . |
| 92/0970 | 11/1992 | South Africa . |
| WO91/07874 | 6/1991 | WIPO . |
| WO91/08202 | 6/1991 | WIPO . |
| WO92/13845 | 8/1992 | WIPO . |
| WO93/17016 | 9/1993 | WIPO . |

OTHER PUBLICATIONS

Official Gazette, Patent Abstract of U.S. Patent No. 5,371,051 published Dec. 6, 1994, p. 425.

*Primary Examiner*—S. Mark Clardy
*Attorney, Agent, or Firm*—Curtis, Morris & Safford, P.C.

[57] ABSTRACT

Herbicide-safener combinations comprising

A) at least one herbicidal active substance from the group of the substituted phenylsulfonylureas of the formula (A) and salts thereof;

in which
$R^1$–$R^4$, W, X, Y, Z and Hal are as defined in claim 1, and

B) at least one compound of the formulae (B1) and (B2)

in which X', W', Z' R* and n' are as defined in claim 1, are suitable as selective herbicidal compositions for use in crop plants, for example in maize, rice, wheat, barley etc.

14 Claims, No Drawings

MIXTURES OF TRIAZINE SULFONYLUREA HERBICIDES AND PYRAZOLINE SAFENERS

The invention relates to the technical field of crop protection products, in particular active substance/antidote combinations (or active substance/safener combinations), which are outstandingly suitable for use against competing harmful plants in crops of useful plants.

Some more recently developed herbicidal active substances display very favorable technical properties in use and can be applied at very low application rates against a wide range of grass weeds and broad-leaf weeds.

However, many of the potent active substances are not fully compatible with (selective in) some important crop plants, such as maize, rice or cereals, so that their use is very limited. This is why they cannot be used in some crops at all, or only at very low application rates which do not guarantee the desired broad herbicidal activity against harmful plants. Specifically, a large number of herbicides of the formula (A) defined further below cannot be employed fully selectively against harmful plants in maize, rice, cereals or some other crops.

Quite unexpectedly, our recent experiments have shown that crop plants such as maize, rice, wheat, barley and others, can be protected against unwanted damage by the above-mentioned herbicides when they are applied together with certain compounds which act as herbicide antidotes or safeners.

The invention therefore relates to herbicide/safener combinations, for example in the form of herbicidal compositions, comprising A) at least one herbicidal active substance selected from the group consisting of substituted phenylsulfonylureas of the formula (A) and salts thereof,

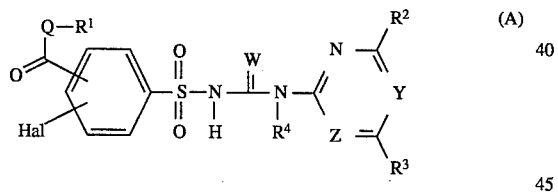

in which

Q is oxygen, sulfur or —N(R)—, where R is H, $(C_1-C_4)$-alkyl or $(C_1-C_4)$-alkoxy, preferably O or S, in particular O;

W is oxygen or sulfur, preferably O;

Y and Z independently of one another are CH or N, where Y and Z are not simultaneously CH, preferably Y is CH or N and Z is N;

$R^1$ is hydrogen; $(C_1-C_{12})$-alkyl; $(C_2-C_{10})$-alkenyl; $(C_2-C_{10})$-alkynyl; $(C_1-C_6)$-alkyl, which is monosubstituted or polysubstituted by identical or different radicals selected from the group consisting of halogen, $(C_1-C_4)$-alkoxy, $(C_1-C_4)$-alkylthio, —CN, $(C_2-C_5)$-alkoxycarbonyl and $(C_2-C_6)$-alkenyl; $(C_3-C_8)$-cycloalkyl which is unsubstituted or substituted by one or more radicals selected from the group consisting of $(C_1-C_4)$-alkyl, $(C_1-C_4)$-alkoxy, $(C_1-C_4)$-alkylthio and halogen; $(C_5-C_8)$-cycloalkenyl; phenyl-$(C_1-C_4)$-alkyl which is unsubstituted or substituted in the phenyl radical; or a radical of the formulae A-1 to A-10,

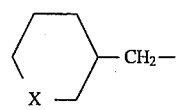

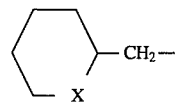

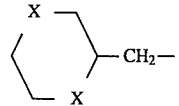

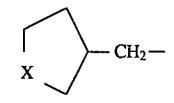

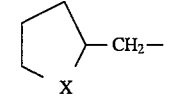

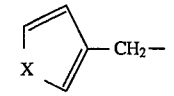

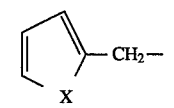

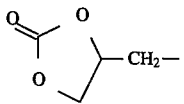

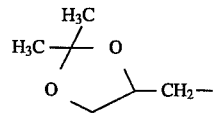

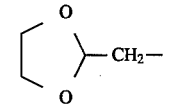

in which

X is O, S, S(O) or $SO_2$, preferably O, $R^2$ is hydrogen, halogen, preferably chlorine, or $(C_1-C_3)$-alkyl or $(C_1-C_3)$-alkoxy, the two last-mentioned radicals being unsubstituted or mono- or poly-substituted by halogen or $(C_1-C_3)$-alkoxy;

$R^3$ is hydrogen, halogen, preferably chlorine, or $(C_1-C_3)$-alkyl, $(C_1-C_3)$-alkoxy or $(C_1-C_3)$-alkylthio, the last-mentioned 3 radicals being unsubstituted or mono- or polysubstituted by halogen or mono- or disubstituted by $(C_1-C_3)$-alkoxy or $(C_1-C_3)$-alkylthio; or a radical of the formula $NR^5R^6$, $(C_3-C_6)$-cycloalkyl, $(C_2-C_4)$-alkenyl, $(C_1-C_4)$-alkynyl, $(C_3-C_4)$-alkenyloxy or $(C_3-C_6)$-alkynyloxy;

$R^4$ is hydrogen or $(C_1-C_4)$-alkyl;

$R^5$ and $R^6$ independently of one another are hydrogen, $(C_1-C_4)$-alkyl, $(C_3-C_4)$-alkenyl, $(C_1-C_4)$-haloalkyl or $(C_1-C_4)$-alkoxy and Hal is fluorine, chlorine, bromine or iodine, and B) at least one compound selected from the group consisting of the compounds of the formulae (B1) and (B2)

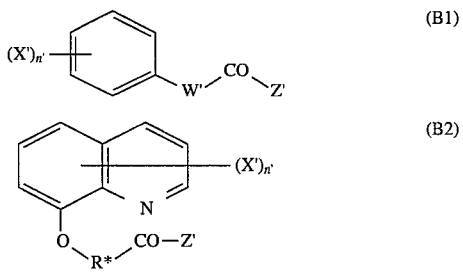

in which

X' is hydrogen, halogen, $(C_1-C_4)$-alkyl, $(C_1-C_4)$-alkoxy, nitro or $(C_1-C_4)$-haloalkyl, Z' is $OR^7$, $SR^7$ or $NR^7R^8$, or is a saturated or unsaturated 3- to 7-membered heterocycle having at least one nitrogen atom and up to 3 hetero atoms which is bonded to the carbonyl group via the nitrogen atom and is unsubstituted or substituted by radicals selected from the group consisting of $(C_1-C_4)$-alkyl, $(C_1-C_4)$-alkoxy or optionally substituted phenyl, preferably by a radical of the formula $OR^7$, $NHR^8$ or $N(CH_3)_2$, in particular of the formula $OR^7$, R* is a ($C_1$ or $C_2$)-alkanediyl chain which can additionally be substituted by one or two $(C_1-C_4)$-alkyl radicals or by $[(C_1-C_3)$-alkoxy]-carbonyl, $R^7$ is hydrogen, $(C_1-C_{18})$-alkyl, $(C_3-C_{12})$-cycloalkyl, $(C_2-C_8)$-alkenyl or $(C_2-C_8)$-alkynyl, the abovementioned carbon-containing radicals being unsubstituted or mono- or polysubstituted, preferably up to trisubstituted by identical or different radicals selected from the group consisting of halogen, hydroxyl, $(C_1-C_8)$-alkoxy, $(C_1-C_8)$-alkylmercapto, $(C_2-C_8)$-alkenylmercapto, $(C_2-C_8)$-alkynylmercapto, $(C_2-C_8)$-alkenyloxy, $(C_2-C_8)$-alkynyloxy, $(C_3-C_7)$-cycloalkyl, $(C_3-C_7)$-cycloalkoxy, cyano, mono- and di- $(C_1-C_4$-alkyl)-amino, carboxyl, $(C_1-C_8)$alkoxycarbonyl, $(C_2-C_8)$-alkenyloxycarbonyl, $(C_1-C_8)$-alkylmercaptocarbonyl, $(C_2-C_8)$-alkynyloxycarbonyl, $(C_1-C_8)$-alkylcarbonyl, $(C_2-C_8)$-alkenylcarbonyl, $(C_2-C_8)$-alkynylcarbonyl, 1-(hydroxyimino)-$(C_1-C_6)$-alkyl, 1-$[(C_1-C_4)$-alkylimino]-$(C_1-C_4)$-alkyl, 1-$[(C_1-C_4)$-alkoxyimino]-$(C_1-C_6)$-alkyl, $(C_1-C_8)$-alkylcarbonylamino, $(C_2-C_8)$-alkenylcarbonylamino, $(C_2-C_8)$-alkynylcarbonylamino, aminocarbonyl, $(C_1-C_8)$-alkylaminocarbonyl, di-$(C_1-C_6)$-alkylaminocarbonyl, $(C_2-C_6)$-alkenylaminocarbonyl, $(C_2-C_6)$-alkynylaminocarbonyl, $(C_1-C_8)$-alkoxycarbonylamino, $(C_1-C_8)$-alkylaminocarbonylamino, $(C_1-C_6)$-alkylcarbonyloxy, which is unsubstituted or substituted by halogen, nitro, $(C_1-C_4)$-alkoxy or optionally substituted phenyl, $(C_2-C_6)$-alkenylcarbonyloxy, $(C_2-C_6)$-alkynylcarbonyloxy, $(C_1-C_8)$-alkylsulfonyl, phenyl, phenyl-$(C_1-C_6)$-alkoxy, phenyl-$(C_1-C_6)$-alkoxycarbonyl, phenoxy, phenoxy-$(C_1-C_6)$-alkoxy, phenoxy-$(C_1-C_6)$-alkoxycarbonyl, phenylcarbonyloxy, phenylcarbonylamino, phenyl-$(C_1-C_6)$-alkylcarbonylamino, the last-mentioned 9 radicals being unsubstituted or mono- or polysubstituted, preferably up to trisubstituted, in the phenyl ring by identical or different radicals selected from the group consisting of halogen, $(C_1-C_4)$-alkyl, $(C_1-C_4)$-alkoxy, $(C_1-C_4)$-haloalkyl, $(C_1-C_4)$-haloalkoxy and nitro, and radicals of the formulae $-SiR'_3$, $-O-SiR'_3$, $R'_3Si-(C_1-C_8)$-alkoxy, $-CO-O-NR'_2$, $-O-N=CR'_2$, $-N=CR'_2$, $-O-NR'_2$, $CH(OR')_2$ and $-O-(CH_2)_m-CH(OR')_2$, where the R' in the above-mentioned formulae independently of one another are hydrogen, $(C_1-C_4)$-alkyl, phenyl which is unsubstituted or mono- or polysubstituted, preferably up to trisubstituted, by identical or different radicals selected from the group consisting of halogen, $(C_1-C_4)$-alkyl, $(C_1-C_4)$-alkoxy, $(C_1-C_4)$-haloalkyl, $(C_1-C_4)$-haloalkoxy and nitro, or, in pairs, are a $(C_2-C_6)$-alkanediyl chain and m is 0 to 6, and a substituted alkoxy radical of the formula R"O—CHR'"(OR")—$(C_1-C_6)$-alkoxy, in which the R" independently of one another are $(C_1-C_4)$-alkyl or together are $(C_1-C_6)$-alkanediyl and R'" is hydrogen or $(C_1-C_4)$-alkyl, $R^8$ is hydrogen, $(C_1-C_6)$-alkyl, $(C_1-C_6)$-alkoxy or optionally substituted phenyl, n' is an integer from 1 to 5, preferably 1 to 3, W' is a divalent heterocyclic radical of one of the formulae (W1) to (W4),

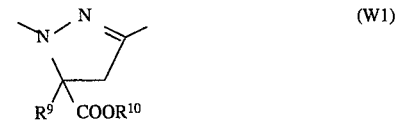

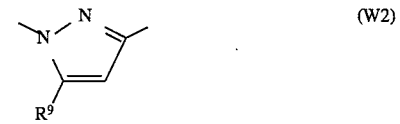

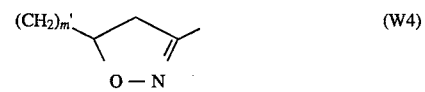

$R^9$ is hydrogen, $(C_1-C_8)$-alkyl, $(C_1-C_8)$-haloalkyl, $(C_3-C_{12})$-cycloalkyl or optionally substituted phenyl, $R^{10}$ is hydrogen, $(C_1-C_8)$-alkyl, $(C_1-C_8)$-haloalkyl, $(C_1-C_4)$-alkoxy-$(C_1-C_4)$-alkyl, $(C_1-C_6)$-hydroxyalkyl, $(C_3-C_{12})$-cycloalkyl or tri-$(C_1-C_4)$-alkylsilyl and m' is 0 or 1.

Unless otherwise defined in specific cases, the following definitions apply to the radicals in the formulae (A), (B1) and (B2):

alkyl, alkenyl and alkynyl are straight-chain or branched and have up to 8, preferably up to 4, carbon atoms; the same applies analogously to the aliphatic moiety of substituted alkyl, alkenyl and alkynyl radicals or to radicals derived therefrom, such as haloalkyl, hydroxyalkyl, alkoxycarbonyl, alkoxy, alkanoyl, haloalkoxy and the like.

Alkyl is, for example, methyl, ethyl, n- and isopropyl, n-, iso-, tert.- and 2-butyl, pentyl radicals, hexyl radicals, such as n-hexyl, isohexyl and 1,3-dimethylbutyl, heptyl radicals, such as n-heptyl, 1-methylhexyl and 1,4-dimethylpentyl. Alkenyl is, for example, allyl, 1-methylprop-2-en-1-yl, but-2-en-1-yl, but-3-en-1-yl, 1-methyl-but-3-en-1-yl and 1-methyl-but-2-en-1-yl. Alkynyl is, for example, propargyl, but-2-yn-1-yl, but-3-yn-1-yl or 1-methyl-but-3-yn-1-yl.

Cycloalkyl has preferably 3 to 8 carbon atoms and is, for example, cyclobutyl, cyclopentyl, cyclohexyl or cycloheptyl. If appropriate, cycloalkyl can have up to two $(C_1-C_4)$-alkyl radicals as substituents.

Halogen is fluorine, chlorine, bromine or iodine, preferably fluorine, chlorine or bromine, in particular fluorine or chlorine. Haloalkyl, haloalkenyl and haloalkynyl are alkyl, alkenyl or alkynyl which are mono-, di-, or polysubstituted by halogen, such as $CF_3$, $CHF_2$, $CH_2F$, $CF_3CF_2$, $CH_2FCHCl$, $CCl_3$, $CHCl_2$ or $CH_2CH_2Cl$. Haloalkoxy is, for example, $OCF_3$, $OCHF_2$, $OCH_2F$, $CF_3CF_2O$ or $CF_3CH_2O$.

Aryl has preferably 6 to 12 carbon atoms and is, for example, phenyl, naphthyl or biphenylyl, but preferably phenyl. The same applies analogously to radicals derived therefrom, such as aryloxy, aroyl or aryloxyalkyl. Optionally substituted phenyl is, for example, phenyl, which is unsubstituted or has one, two or three identical or different substituents selected from the group consisting of halogen, $(C_1-C_4)$-alkyl, $(C_1-C_4)$-alkoxy, $(C_1-C_4)$-haloalkyl, $(C_1-C_4)$-haloalkoxy, $(C_1-C_4)$-alkylthio, $(C_2-C_5)$-alkoxycarbonyl, $(C_2-C_5)$-alkylcarbonyloxy, carboxamide, $(C_2-C_5)$-alkylcarbonylamino, $(C_2-C_5)$-alkylaminocarbonyl, Di[$(C_1-C_4)$-alkyl]-aminocarbonyl and nitro, such as, for example, o-, m- and p-tolyl, dimethylphenyl radicals, 2-, 3- and 4-chlorophenyl, 2-, 3- and 4-trifluoro- and -trichlorophenyl, 2,4-, 3,5-, 2,5- and 2,3-dichlorophenyl or o-, m- and p-methoxyphenyl. The same applies analogously to optionally substituted aryl.

The compounds of the formula (A) can form salts in which the hydrogen of the $-SO_2-NH-$ group is replaced by an agriculturally suitable cation. Examples of these salts are metal salts, in particular alkali metal salts (for example sodium or potassium salts) or alkaline earth metal salts, or else ammonium salts or salts with organic amines. Equally, salt formation can take place by an addition reaction of a strong acid with the heterocycle moiety of the compounds of the formula (A). Acids which are suitable for this purpose are, for example, HCl, $HNO_3$, trichloroacetic acid, acetic acid or palmitic acid.

In the following text, herbicide (A) is to be understood as meaning the compounds of the formula (A) and the salts thereof.

Some compounds of the formula (A), (B1) or (B2) can contain one or more asymmetric carbon atoms or else double bonds, which are not specifically indicated in the formulae. The stereoisomers which are possible and which are defined by their specific spatial shape, such as enantiomers, diastereomers, Z and E isomers, are, however, all embraced by the formulae and can be obtained from the stereoisomer mixtures by customary methods or else prepared by stereoselective reactions in combination with the use of stereochemically pure starting substances. Thus, the abovementioned stereoisomers can be employed according to the invention in pure form and in the form of their mixtures.

Herbicide/safener combinations according to the invention which are of particular interest are those with compounds of the formula (A) or salts thereof, in which $R^1$ is hydrogen; $(C_1-C_6)$-alkyl; $(C_2-C_6)$-alkenyl; $(C_2-C_6)$-alkynyl; $(C_1-C_4)$-alkyl which can be monosubstituted to tetrasubstituted, preferably monosubstituted, by radicals selected from the group consisting of halogen, $(C_1-C_2)$-alkoxy, $(C_1-C_2)$-alkylthio, $(C_2-C_3)$-alkoxycarbonyl and $(C_2-C_4)$-alkenyl; $(C_5-C_6)$-cycloalkyl which is unsubstituted or substituted by one or more radicals selected from the group consisting of $(C_1-C_4)$-alkyl, $(C_1-C_4)$-alkoxy, $(C_1-C_4)$-alkylthio and halogen; $(C_5-C_6)$-cycloalkenyl; benzyl which is unsubstituted or substituted in the phenyl moiety by one to three radicals selected from the group consisting of halogen, $(C_1-C_2)$-alkyl, $(C_1-C_2)$-alkoxy, $(C_1-C_2)$-haloalkyl, $(C_1-C_2)$-alkylthio and $(C_2-C_4)$alkoxycarbonyl, or a radical of the abovementioned formulae A-1 to A-10 and Hal is chlorine, bromine or iodine.

Other herbicide/safener combinations according to the invention which are of particular interest are those with compounds of the formula (A) or salts thereof, in which $R^2$ is hydrogen, halogen, preferably chlorine, $(C_1-C_2)$-alkyl, $(C_1-C_2)$-alkoxy, the two last-mentioned radicals being unsubstituted or mono- or polysubstituted by halogen or $(C_1-C_3)$-alkoxy;

$R^3$ is hydrogen, halogen, or preferably chlorine, $(C_1-C_2)$-alkyl, $(C_1-C_2)$-alkoxy or $(C_1-C_2)$-alkylthio, the abovementioned alkyl-containing radicals being unsubstituted or mono- or polysubstituted by halogen or mono- or disubstituted by $(C_1-C_2)$-alkoxy or $(C_1-C_2)$-alkylthio; or a radical of the formula $NR^5R^6$;

$R^4$ is hydrogen or methyl, $R^5$ and $R^6$ independently of one another are hydrogen or $(C_1-C_2)$-alkyl and Hal is chlorine or iodine.

Preferred herbicide/safener combinations according to the invention are those with compounds of the formula (A) or salts thereof, in which W is an oxygen atom, Y is CH or N, Z is N $R^2$ is hydrogen, $CH_3$, $CH_2CH_3$, $OCH_3$, $OCH_2CH_3$, $OCHF_2$ or Cl, $R^3$ is hydrogen, $CH_3$, $CH_2CH_3$, $OCH_3$, $OCH_2CH_3$, $OCHF_2$, $NH(CH_3)$, $N(CH_3)_2$, $CF_3$, $OCH_2CF_3$ or Cl, $R^4$ is H or $CH_3$ and Hal is iodine.

Other herbicidal compositions which are of particular interest are those in which, in formula (B1) or (B2), $R^7$ is hydrogen, $(C_1-C_8)$-alkyl or $(C_3-C_7)$-cycloalkyl, the abovementioned carbon-containing radicals being unsubstituted or mono- or polysubstituted by halogen or mono- or disubstituted, preferably up to monosubstituted, by radicals selected from the group consisting of hydroxyl, $(C_1-C_4)$-alkoxy, carboxyl, $(C_1-C_4)$-alkoxycarbonyl, $(C_2-C_6)$-alkenyloxycarbonyl, $(C_2-C_6)$-alkynyloxycarbonyl, 1-(hydroxyimino)-$(C_1-C_4)$-alkyl, 1-[$(C_1-C_4)$-alkylimino]-$(C_1-C_4)$-alkyl, 1-[$(C_1-C_4)$-alkoxyimino]-$(C_1-C_4)$-alkyl, and radicals of the formulae $-SiR'_3$, $-O-N=CR'_2$, $-N=CR'_2$ and $-O-NR'_2$, where the R' in the abovementioned formulae independently of one another are hydrogen or $(C_1-C_4)$-alkyl or, in pairs, are a $(C_4-C_5)$-alkanediyl chain, $R^9$ is hydrogen, $(C_1-C_8)$-alkyl, $(C_1-C_6)$-haloalkyl, $(C_3-C_7)$-cycloalkyl or phenyl and $R^{10}$ is hydrogen, $(C_1-C_8)$-alkyl, $(C_1-C_8)$-haloalkyl, $(C_1-C_4$-alkoxy)-$(C_1-C_4)$-alkyl, $(C_1-C_6)$-hydroxyalkyl, $(C_3-C_7)$-cycloalkyl or tri-$(C_1-C_4)$-alkylsilyl, and herbicidal compositions in which, in formula (B1) or (B2), X' is hydrogen, halogen, methyl, ethyl, methoxy, ethoxy, ($C_1$ or $C_2$)-haloalkyl, preferably hydrogen, halogen or ($C_1$ or $C_2$)-haloalkyl.

Preferred herbicidal compositions are those in which, in formula (B1),

X' is hydrogen, halogen, nitro or $(C_1-C_4)$-haloalkyl, n' is 1, 2 or 3,

Z' is a radical of the formula $OR^7$, $R^7$ is hydrogen, $(C_1-C_8)$-alkyl or $(C_3-C_7)$-cycloalkyl, where the abovementioned carbon-containing radicals are unsubstituted or mono- or polysubstituted, preferably up to trisubstituted, by identical or different halogen radicals or up to disubstituted, preferably up to monosubstituted, by identical or different radicals selected from the group consisting of hydroxyl, $(C_1-C_4)$-alkoxy, $(C_2-C_4)$-alkoxycarbonyl, $(C_2-C_6)$-alkenyloxycarbonyl, $(C_2-C_6)$-alkynyloxycarbonyl, 1-(hydroxyimino)-$(C_1-C_4)$alkyl, 1-[$(C_1-C_4)$-alkylimino]-$(C_1-C_4)$-alkyl, 1-[$(C_1-C_4)$-alkoxyimino]-$(C_1-C_4)$-alkyl and radicals of the formulae —$SiR'_3$, —O—N=$R'_2$, —N=$CR'_2$ and —O—$NR'_2$, where the radicals R' in the abovementioned formulae independently of one another are hydrogen or $(C_1-C_4)$-alkyl or, in pairs, are $(C_4$ or $C_5)$-alkanediyl, $R^9$ is hydrogen, $(C_1-C_8)$-alkyl, $(C_1-C_6)$-haloalkyl, $(C_3-C_7)$-cycloalkyl or phenyl and is hydrogen, $(C_1-C_8)$-alkyl, $(C_1-C_8)$-haloalkyl, $(C_1-C_6)$-alkoxy-$(C_1-C_4)$-alkyl, $(C_1-C_6)$-hydroxyalkyl, $(C_3-C_7)$-cycloalkyl or tri-$(C_1-C_4)$-alkylsilyl.

Other preferred herbicidal compositions are those in which in formula (B2),

X' is hydrogen, halogen or $(C_1-C_4)$-haloalkyl, n' is 1, 2 or 3, where $(X')_{n'}$ is preferably 5-Cl, Z' is a radical of the formula $OR^7$, R* is $CH_2$ and $R^7$ is hydrogen, $(C_1-C_8)$-alkyl, $(C_1-C_8)$-haloalkyl or $(C_1-C_4)$-alkoxy-$(C_1-C_4)$-alkyl, preferably $(C_1-C_8)$-alkyl.

Particularly preferred herbicidal compositions are those in which, in formula (B1), W' is (W1), X' is hydrogen, halogen or $(C_1-C_2)$haloalkyl, n' is 1, 2 or 3, where $(X')_{n'}$ is preferably 2,4-$Cl_2$, Z' is a radical of the formula $OR^7$, $R^7$ is hydrogen, $(C_1-C_8)$-alkyl, $(C_1-C_4)$-haloalkyl, $(C_1-C_4)$-hydroxyalkyl, $(C_3-C_7)$-cycloalkyl, $C_1-C_4$)-alkoxy-$(C_1-C_4)$-alkyl, tri-$(C_1-C_2)$-alkylsilyl, preferably $(C_1-C_4)$-alkyl, $R^9$ is hydrogen, $(C_1-C_8)$-alkyl, $(C_1-C_4)$-haloalkyl or $(C_3-C_7)$-cycloalkyl, preferably hydrogen or $(C_1-C_4)$-alkyl and $R^{10}$ is hydrogen, $(C_1-C_8)$-alkyl, $(C_1-C_4)$-haloalkyl, $(C_1-C_4)$-hydroxyalkyl, $(C_3-C_7)$-cycloalkyl, $(C_1-C_4)$-alkoxy-$(C_1-C_4)$-alkyl or tri-$(C_1-C_2)$-alkylsilyl, preferably hydrogen or $(C_1-C_4)$-alkyl.

Other particularly preferred herbicidal compositions are those in which in formula (B1), W' is (W2), X' is hydrogen, halogen or $(C_1-C_2)$-haloalkyl, n' is 1, 2 or 3, where $(X')_{n'}$ is preferably 2,4-$Cl_2$, Z' is a radical of the formula $OR^7$, $R^7$ is hydrogen, $(C_1-C_8)$-alkyl, $(C_1-C_4)$-haloalkyl, $(C_1-C_4)$-hydroxyalkyl, $(C_3-C_7)$-cycloalkyl, $(C_1-C_4$-alkoxy)-$C_1-C_4$-alkyl, tri-$(C_1-C_2)$-alkyl-silyl, preferably $(C_1-C_4)$-alkyl and $R^9$ is hydrogen, $(C_1-C_8)$-alkyl, $(C_1-C_4)$-haloalkyl, $(C_3-C_7)$-cycloalkyl or phenyl, preferably hydrogen or $(C_1-C_4)$-alkyl.

Other particularly preferred herbicidal compositions are those in which, in formula (B1), W' is (W3), X' is hydrogen, halogen or $(C_1-C_2)$-haloalkyl, n' is 1, 2 or 3, where $(X')_{n'}$ is preferably 2,4-$Cl_2$, Z' is a radical of the formula $OR^7$, $R^7$ is hydrogen, $(C_1-C_8)$-alkyl, $(C_1-C_4)$-haloalkyl, $(C_1-C_4)$-hydroxyalkyl, $(C_3-C_7)$-cycloalkyl, $(C_1-C_4)$-alkoxy-$(C_1-C_4)$-alkyl, tri-$(C_1-C_2)$-alkylsilyl, preferably $(C_1-C_4)$-alkyl and $R^9$ is $(C_1-C_8)$-alkyl or $(C_1-C_4)$-haloalkyl, preferably $C_1$-haloalkyl.

Other particularly preferred herbicidal compositions are those in which, in formula (B1), W' is (W4), X' is hydrogen, halogen, nitro, $(C_1-C_4)$-alkyl or $(C_1-C_2)$-haloalkyl, preferably $CF_3$ or $(C_1-C_4)$-alkoxy, n' is 1, 2 or 3, m' is 0 or 1, Z' is a radical of the formula $OR^7$ and $R^7$ is hydrogen, $(C_1-C_4)$-alkyl, carboxyl-$(C_1-C_4)$-alkyl or $(C_1-C_4)$-alkoxycarbonyl-$(C_1-C_4-)$-alkyl, preferably $(C_1-C_4)$-alkoxy-CO—$CH_2$—, $(C_1-C_4)$-alkoxy-CO—$C(CH_3)H$—, HO—CO—$CH_2$— or HO—CO—$C(CH_3)H$—.

The compounds of the formulae (B1) are known from EP-A-333 131 (ZA-89/1960), EP-A-269 806 (U.S. Pat. No. 4,891,057), EP-A-346 620 (AU-A-89/34951) and the international patent applications PCT/EP 90/01966 (WO-91/08202) and PCT/EP 90/02020 (WO-91/07874) and the literature cited therein or can be prepared by, or analogously to, the processes described in these publications. The compounds of the formula (B2) are known from EP-A-94 349 (U.S. Pat. No. 4,902,340), EP-A-191 736 (U.S. Pat. No. 4,881,966) and EP-A-0 492 366 and the literature cited in these publications or can be prepared by, or analogously to, the processes described in these publications. Some compounds are furthermore described in German Patent Application P 42 25 493.0.

Suitable herbicidal active substances according to the invention are those pyrimidine or triazine derivatives of the formula (A) which, on their own, cannot be applied, or not optimally applied, in cereal crops and/or in maize because they inflict too much damage on crop plants.

The compounds of the formula (A) are known, for example, from EP-A-007 687, EP-A-0291851, DE-A-7900472, U.S. Pat. No. 4,566,898 and WO 92/13845 or can be prepared analogously to the processes mentioned in these publications.

The following groups of compounds have proved themselves as safeners for the abovementioned herbicidal active substances:

a) Compounds of the dichlorophenylpyrazoline-3-carboxylic acid type (i.e. of the formula (B1) in which W' is W1 and $(X')_{n'}$=2.4-$Cl_2$), preferably compounds such as ethyl 1-(2,4-dichlorophenyl)-5-(ethoxycarbonyl)-5-methyl-2-pyrazoline-3-carboxylate (B1-1) and related compounds as they are described in WO 91/07874.

b) Dichlorophenylpyrazolecarboxylic acid derivatives (i.e. of the formula (B1) in which W' is W2 and $(X')_{n'}$ is 2,4-$Cl_2$), preferably compounds such as ethyl 1-(2, 4-dichlorophenyl)-5-methylpyrazole-3-carboxylate (B1-2), ethyl 1-(2,4-dichlorophenyl)-5-isopropylpyrazole-3-carboxylate (B1-3), ethyl 1-(2,4-dichlorophenyl)-5-(1,1-dimethylethyl)pyrazole-3-carboxylate (B1-4), ethyl 1-(2,4-dichlorophenyl)-5-phenylpyrazole-3-carboxylate (B1-5) and related compounds as they are described in EP-A-333 131 and EP-A-269 806.

c) Compounds of the triazolecarboxylic acid type (i.e. of the formula (B1) in which W' is W3 and $(X')_{n'}$ is 2.4-Cl$_2$), preferably compounds such as fenchlorazole, i.e. ethyl 1-(2,4-dichlorophenyl)-5-trichloromethyl-(1H)-1,2,4-triazole-3-carboxylate (B1-6), and related compounds (see EP-A 174 562 and EP-A-346 620).

d) Compounds of the 5-benzyl-or 5-phenyl-2-isoxazoline-3-carboxylic acid type, preferably compounds such as ethyl 5-(2,4-dichlorobenzyl)-2-isoxazoline-3-carboxylate (B1-7) or ethyl 5-phenyl-2-isoxazoline-3-carboxylate (B1-8), and related compounds as described in WO 91/08202.

e) Compounds of the 8-quinolineoxyacetic acid type, for example those of the formula (B2) in which $(X')_{n'}$ is 5-Cl, hydrogen, Z' is OR$^7$, R$^*$ is CH$_2$), preferably compounds such as
1-methylhex-1-yl (5-chloro-8-quinolineoxy) acetate (B2-1),
1,3-dimethylbut-1-yl 5-chloro-8-quinolineoxy)acetate (B2-2),
4-allyloxybutyl (5-chloro-8-quinolineoxy)acetate (B2-3),
1-allyloxyprop-2-yl (5-choloro-8-quinolineoxy)acetate (B2-4),
ethyl (5-chloro-8-quinolineoxy)acetate (B2-5),
methyl (5-chloro-8quinolineoxy)acetate (B2-6),
allyl (5-chloro-8-quinolineoxy)acetate (B2-7),
2-(2-propylideneiminoxy)-1-ethyl (5-chloro-8-quinolineoxy)acetate (B2-8), and
2-oxoprop-1-yl (5-chloro-8-quinolineoxy)acetate (B2-9)
and related compounds as described in EP-A-86 750, EP-A-94 349 and EP-A-191 736 or EP-A-0 492 366.

f) Compounds of the (5-chloro-8-quinolineoxy)malonic acid type (i.e. of the formula (B2) in which $(X')_{n'}$ is 5-Cl, Z' is OR$^7$, R$^*$ is —CH(COO—alkyl)-, preferably compounds such as diethyl (5-chloro-8-quinolineoxy)malonate, diallyl (5-chloro-8-quinolineoxy)malonate, methyl ethyl (5-chloro-8-quinolineoxy)malonate and related compounds as described in German Patent Application P 42 25 493.0.

g) Active substances of the phenoxyacetic or -propionic acid derivative type or of the aromatic carboxylic acid type such as, for example, 2,4-dichlorophenoxyacetic acid (ester) (2,4-D), 4-chloro-2-methylphenoxypropionic ester (mecoprop), MCPA or 3,6-dichloro-2-methoxybenzoic acid (ester) (dicamba).

The safeners (antidotes) of the formulae (B1) and (B2) and, for example, of the above groups a) to g) reduce, or prevent, phytotoxic effects which can occur when applying the herbicidal active substances of the formula (A) to crops of useful plants without adversely affecting the efficacy of these herbicidal active substances against harmful plants. This allows the field of application of conventional crop protection products to be widened quite considerably and to be extended, for example, to crops such as wheat, barley, maize and other Gramineae crops in which application of the herbicides has not been possible as yet or only to a limited extent, that is to say at low dosage rates with a low degree of broad-range action.

The herbicidal active substances and the abovementioned safeners can be applied together (as a readymix or by the tank mix method) or one after the other, in any desired sequence. The ratio by weight of safener: herbicidal active substance can vary within wide limits and is preferably in a range of 1:100 to 100:1, in particular 1:10 to 10:1. The amounts of herbicidal active substance and safener which are optimal in each case will depend on the type of the herbicidal active substance used or on the safener used and on the species of the plant stock to be treated and can be determined in each individual case by suitable preliminary experiments.

The safeners are mainly applied in particular in maize and cereal crops (wheat, rye, barley, oats), rice, sorghum, but also cotton and soybeans, preferably in cereals and maize.

Depending on their properties, the safeners of the formulae (B1) and (B2) can be used for pre-treating seed of the crop plant (seed dressing), or they can be incorporated into the seed farrows prior to sowing, or used together with the herbicide prior to, or after, plant emergence. Pre-emergence treatment includes both the treatment of the area under cultivation prior to sowing and treatment of the areas under cultivation where seed has been sown, but growth of the crop plants has not yet taken place. The joint application together with the herbicide is preferred. Tank mixes or ready-mixes can be employed for this purpose. The application rates of safener required can vary within wide limits, depending on the indication and the herbicidal active substance used, and, as a rule, they range from 0.001 to 5 kg, preferably 0.005 to 0.5 kg, of active substance per hectare.

The present invention therefore also relates to a method of protecting crop plants against phytotoxic side-effects of herbicides of the formula (A), which comprises applying an effective amount of a compound of the formula (B1) and/or (B2) to the plants, the seeds of the plants or the area under cultivation either before, after or simultaneously with, the herbicidal active substance of the formula (A).

The compounds of the formulae (B1) and (B2) and their combinations with one or more of the abovementioned herbicidal active substances can be formulated in a variety of ways, as predetermined by the biological and/or chemicophysical parameters. The following possibilities are therefore examples suitable for formulation: wettable powders (WP), emulsifiable concentrates (EC), water-soluble powders (SP), water-soluble concentrates (SL), concentrated emulsions (BW) such as oil-in-water and water-in-oil emulsions, sprayable solutions or emulsions, capsule suspensions (CS), oil- or water-based dispersions (SC), suspoemulsions, suspension concentrates, dusts (DP), oil-miscible solutions (OL), seed-dressing products, granules (GR) in the form of microgranules, spray granules, coated granules and adsorption granules, granules for soil application or for broadcasting, water-soluble granules (SG), water-dispersible granules (WG), ULV formulations, micro-capsules and waxes.

These individual types of formulation are known in principle and are described, for example, in: Winnacker-Küchler, "Chemische Technologie" [Chemical Technology], Volume 7, C. Hauser Verlag Munich, 4th Ed. 1986; Wade van Valkenburg, "Pesticide Formulations", Marcel Dekker N.Y., 1973; K. Martens, "Spray Drying Handbook", 3rd Ed. 1979, G. Goodwin Ltd. London.

The formulation auxiliaries required, such as inert materials, surfactants, solvents and other additives, are also known and are described, for example, in: Watkins, "Handbook of Insecticide Dust Diluents and Carriers", 2nd Ed., Darland Books, Caldwell N.J.; H. v. Olphen "Introduction to Clay Colloid Chemistry", 2nd Ed., J. Wiley & Sons, N.Y., Marsden "Solvents Guide, 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc. N.Y. 1964; Schönfeldt, "Grenzflächenaktive Äthylenoxidaddukte", [Surface-Active Ethylene Oxide Adducts], Wiss. Verlagsgesell., Stuttgart 1976; Winnacker-Küchler "Chemische Technolgie", [Chemical Technology], Volume 7, C. Hauser Verlag Munich, 4th Ed. 1986.

Combinations with other pesticidally active substances, fertilizers and/or growth regulators may also be prepared on the basis of these formulation, for example in the form of a readymix or a tank mix.

Wettable powders are preparations which are uniformly dispersible in water and which, besides the active substances, also contain ionic and/or nonionic surfactants (wetting agents, dispersants), for example polyoxethylated alkylphenols, polyoxethylated fatty alcohols and fatty amines, fatty alcohol polyglycol ether sulfates, alkanesulfonates or alkylarylsulfonates, sodium ligninsulfonate, sodium 2,2'-dinaphthylmethane-6-6'-disulfonate, sodium dibutylnaphthalinesulfonate or else sodium oleylmethyltaurinate, in addition to a diluent or inert substance.

Emulsifiable concentrates are prepared by dissolving the active substance, or the active substances, in an organic solvent, for example butanol, cylcohexanone, dimethylformamide, xylene or else higher-boiling aromatics or hydrocarbons with the addition of one or more ionic or non-ionic surfactants (emulsifiers). Examples of emulsifiers which can be used are: calcium alkylarylsulfonates, such as calcium dodecylbenzenesulfonate, or nonionic emulsifiers, such as fatty acid polyglycol esters, alkylaryl polyglycol ethers, fatty alcohol polyglycol ethers, propylene oxide/ethylene oxide condensation products (for example block polymers), alkyl polyethers, sorbitan fatty acid esters, polyoxyethylene sorbitan fatty acid esters, or other polyoxyethylene sorbitan esters.

Dusts are obtained by grinding the active substance, or the active substances, together with finely divided solid substances, for example talc, natural clays, such as kaolin, bentonite and pyrophyllite or diatomacesus earth.

Granules can be produced either by spraying the active substance, or the active substances, onto adsorbtive, granulated inert material, or by applying active substance concentrates to the surface of carriers, such as sand, kaolinites or granulated inert material, by means of binders, for example polyvinyl alcohol, sodium polyacrylate or else mineral oils. As a rule, water-dispersible granules are produced by the customary processes such as spray drying, fluidized-bed granulation, disc granulation, mixing using high-speed stirrers, and extrusion without solid inert material. Suitable active substances can also be granulated in the manner which is conventional for the production of fertilizer granules, if desired in the form of a mixture with fertilizers.

As a rule, the agrochemical preparations comprise 0.1 to 99% by weight, in particular 0.1 to 95% by weight, of active substances of the formula (B1) and/or (B2) or of the herbicide/antidote active substance mixture (A) and (B1) and/or (B2), and 1 to 99.9% by weight, in particular 5 to 99.8% by weight, of a solid or liquid additive and 0 to 25% by weight, in particular 0.1 to 25% by weight, of a surfactant.

In wettable powders, the active substance concentration is, for example, approximately 10 to 90% by weight, the remainder to 100% by weight being composed of conventional formulation components. In the case of emulsifiable concentrates, the active substance concentration is approximately 1 to 80% by weight. Formulations in the form of dusts usually comprise approximately 1 to 20% by weight of active substances, sprayable solutions approximately 0.2 to 20% by weight of active substances. In the case of granules, such as water-dispersible granules, the active substance content will partly depend on whether the active compound is in liquid or solid form. As a rule, the water-dispersible granules comprise between 10 and 90% by weight of active substance.

In addition, the active substance formulations mentioned comprise, if appropriate, the adhesives, wetting agents, dispersants, emulsifiers, penetrants, solvents, fillers or carriers which are conventional in each case.

For use, the formulations, present in commercially available form, are diluted, if appropriate, in a customary manner, for example using water in the case of wettable powders, emulsifiable concentrates, dispersions and water-dispersible granules. Preparations in the form of dusts, granules and sprayable solutions are conventionally not further diluted with other inert substances before use. Particularly high rates of efficacy of the compositions according to the invention can be achieved when the tank mix method is used for adding further wetting agents at concentrations of 0.1 to 0.5% by weight in addition to the surfactants present in the formulations, for example non-ionic wetting agents or wetting agents of the fatty alcohol polyol ether sulfate type (see, for example, German Patent Application P 40 29 304.1) The application rate of the safeners required varies with the external conditions such as, inter alia, temperature, humidity and the nature of the herbicide used.

Based on these formulations, it is also possible to produce combinations with other substances which are active in crop cultivation, for example pesticides, such as insecticides, acaricides, fungicides and herbicides, and/or fertilizers and/or growth regulators, for example in the form of a ready-mix or a tank mix.

Components which can be used in combination with the active substances according to the invention in mixed formulations or in tank mixes are, for example, known active substances, as they are described, for example, in Weed Research 26, 441–445 (1986), or "The Pesticide Manual", 9th edition, The British Crop Protection Council, 1990/91, Bracknell, England, and the literature cited therein. Examples of active substances which may be mentioned as herbicides which are known from the literature which can be combined with the compounds of the formula (I) are the following (note: either the common names in accordance with the International Organization for Standardization (ISO) or the chemical names, if appropriate together with a customary code number, of the compounds are given): acetochlor; acifluorfen; aclonifen; AKH 7088, i.e. [[[1-[5-[2-chloro-4-(trifluoromethyl)phenoxy]-2-nitrophenyl]-2-methoxy ethylidene]amino]oxy]acetic acid and its methyl ester; alachlor; alloxydim; ametryn; amidosulfuron; amitrol; AMS, i.e. ammonium sulfamate; anilofos; asulam; atrazine; aziprotryn; barban; BAS 516 H, i.e. 5-fluoro-2-phenyl-4H-3,1-benzoxazin-4-one; benazolin; benfluralin; benfuresate; bensulfuron-methyl; bensulide; bentazone; bezofenap; benzofluor; benzoylprop-ethyl; benzthiazuron; bialaphos; bifenox; bromacil; bromobutide; bromofenoxim; bromoxynil; bromuron; buminafos; busoxinone; butachlor; butamifos; butenachlor; buthidazole; butralin; butylate; carbetamide; CDAA, i.e. 2-chloro-N,N-di-2-propenyl-acetamide; CDEC, i.e. 2-chloroallyl diethyldithiocarbamate; CGA 184927, i.e. 2-[4-[(5-chloro-3-fluoro-2-pyridinyl)oxy]phenoxy]propanoic acid and its 2-propynyl ester; chlomethoxyfen; chloramben; chlorazifop-butyl, pirifenop-butyl; chlorbromuron; chlorbufam; chlorfenac; chlorflurecol-methyl; chloridazon; chlorimuron ethyl; chlornitrofen; chlorotoluron; chloroxuron; chlorpropham; chlorsulfuron; chlorthaldimethyl; chlorthiamid; cinmethylin; cinosulfuron; clethodim; clomazone; clomeprop; cloproxydim; clopyralid; cyanazine; cycloate; cycloxydim; cycluron; cyperquat; cyrprazine; cyprazole; 2,4-DB; dalapon; desmedipham; desmetryn; di-allate; dicamba; dichlobenil; dichlorprop; diclofop-methyl; diethatyl; difenoxuron; difenzoquat; diflufenican; dimefuron; dimethachlor; dimethametryn; dimethazone; clomazon; dimethipin; dimetrasulfuron; cinosulfuron; dinitramine; dinoseb; dinoterb; diphenamid; dipropetryn; diquat; dithiopyr; diuron; DNOC; eglinazine-ethyl; EL 177, i.e. 5-cyano-1-(1,1-dimethylethyl)-N-methyl-3H-pyrazole-4-carboxamide; endothal; EPTC; esprocarb; ethalfluralin; ethametsulfuron-methyl; ethidimuron; ethiozin; ethofumesate; F5231; i.e. N-[2-chloro-4-fluoro-5-[4-(3-fluoropropyl)-4,5-dihydro-5-oxo-1H-tetrazol-1-yl]phenyl]-ethanesulfonamide; F6285; i.e. 1-[5-(N-methylsulfonyl)-amino-2,4-dichlorophenyl] -3methyl-4-difluoromethyl-1,2,4-triazol-5one; fenoprop; fenoxan; clomazon; fenxoaprop-ethyl; fenuron; flamprop-methyl; flazasulfuron; fluazifop and its ester derivatives; fluchloralin; flumetsulam; N-[2,6-difluorophenyl]-5-methyl-(1,2,4)-triazolo[1,5a]pyrimidine-2-sulfonamide; flumeturon; flumipropyn; fluorodifen; fluoroglycofenethyl; fluridone; fluorochloridone; fluroxypyr; flurtamone; fomesafen; fosamine; furyloxyfen; glufosinate; glyphosate; halosafen; haloxyfop and its ester derivatives; hexazinone; Hw 52, i.e. N-(2,3-dichlorophenyl)-4-(ethoxymethoxy)benzamide; imazamethabenzmethyl; imazapyr; imazaquin; imazethamethapyr; imazethapyr; imazosulfuron; ioxynil; isocarbamide; isopropalin; isoproturon; isouron; isoxaben; isoxapyrifop; karbutilate; lactofen; lenacil; linuron; MCPA; MCPB; mecoprop; mefenacet; mefluidid; metamitron; metazachlor; methabenzthiazuron; metham; methazole; methoxyphenone; methyldaimuron; metobromuron; metolachlor; metoxuron; metribuzin; metsulfuron-methyl; MH; molinate; monalide; monocarbamide dihydrogensulfate; monolinuron; monuron; MT 128, i.e. 6-chloro-N-(3-chloro-2-propenyl)-5-methyl-N-phenyl-3-pyridazineamine; MT 5950, i.e. N-[3-chloro-4-(1-methylethyl)phenyl]-2-methyl-pentaneamide; naproanilide; napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiazon; oxyfluorfen; paraquat; pebulate; pendimethalin; perfluidone; phenmedipham; phenisopham; phenmedipham; picloram; piperophos; piributicarb; pirifenop-butyl; pretilachlor; primisulfuron-methyl; procyazine; prodiamine; profluralin; proglinazine-ethyl; prometon; prometryn; propachlor; propanil; propaquizafop and its ester derivatives; propazine; propham; propyzamide; prosulfalin; prosulfocarb; prynachlor; pyrazolinate; pyrazon; pyrazosulfuron-ethyl; pyrazoxyfen; pyridate; quinclorac; quinmerac; quinofop and its ester derivatives, quizalofop and its ester derivatives; quizalofop-ethyl; quizalofop-p-tefuryl; renriduron; dymron; S 275, i.e. 2-[4-chloro-2-fluoro-5-(2-propynyloxy)phenyl]-4,5,6,7-tetrahydro-2H-indazole; S 482, i.e. 2-[7-fluoro-3,4-dihydro-3-oxo-4-(2-propynyl)-2H-1,4-benzoxazin-6-yl]-4,5,6,7-tetrahydro-1H-isoindole-1,3(2H)-dione; secbumeton; sethoxydim; siduron; simazine; simetryn; SN 106279, i.e. 2-[[7-[2-chloro-4-(trifluoromethyl)phenoxy]-2-naphthalenyl]oxy]propanoic acid and its methyl ester; sulfometuron-methyl; sulfazuron; flazasulfuron; TCA; tebutam; tebuthiuron; terbacil; terbucarb; terbuchlor; terbumeton; terbuthylazine; terbutryn; TFH 450, i.e. N,N-diethyl-3-[(2-ethyl-6-methylphenyl)-sulfonyl]-1H-1,2,4-triazole-1-carboxamide; thiazafluron; thifensulfuron-methyl; thiobencarb; tiocarbazil; tralkoxydim; tri-allate; triasulfuron; triazofenamide; tribenuron-methyl; triclopyr; tridiphane; trietazine; trifluralin; trimeturon; vernolate; WL 110547; i.e. 5-phenoxy-1-[3-(trifluoromethyl)phenyl]-1H-tetrazole.

The application rate required for the compounds of the formula (A) according to the invention varies with the external conditions such as, inter alia, temperature, humidity and nature of the herbicide used. It can be varied within wide limits, for example between 0.001 and 10.0 kg/ha or more of active ingredient, but it is preferably between 0.005 and 5 kg/ha.

The examples which follow are intended to illustrate the invention:

A. Formulation examples a) A dust is obtained by mixing 10 parts by weight of a compound of the formula (B1) and/or (B2) or of an active substance mixture of a herbicidal active substance of the formula (A) and a safener of the formula (B1) and/or (B2) and 90 parts by weight of talc as inert substance and comminuting the mixture in a hammer mill.

b) A wettable powder which is readily dispersible in water is obtained by mixing 25 parts by weight of a compound of the formula (B1) and/or (B2) or of an active substance mixture of a herbicidal active substance of the formula (A) and a safener of the formula (B1) and/or (B2), 64 parts by weight of kaolin-containing quarz as inert substance, 10 parts by weight of potassium ligninsulfonate and 1 part by weight of sodium oleoylmethyltaurinate as wetting and dispersing agent, and grinding the mixture in a pinned-disc mill.

c) A dispersion concentrate which is readily dispersible in water is obtained by mixing 20 parts by weight of a compound of the formula (B1) and/or (B2) or of an active substance mixture of a herbicidal active substance of the formula (A) and a safener of the formula (B1) and/or (B2), 6 parts by weight of alkylphenol polyglycol ether (Triton® X 207), 3 parts by weight of isotridecanol polyglycol ether (8 EO) and 71 parts by weight of paraffinic mineral oil (boiling range for example approximately 255 to above 277° C.), and grinding the mixture in a ball mill to a fineness of below 5 microns.

d) An emulsifiable concentrate is obtained from 15 parts by weight of a compound of the formula (B1) and/or (B2) or of an active substance mixture of a herbicidal active substance of the formula (A) and a safener of the formula (B1) and/or (B2), 75 parts by weight of cyclohexanone as solvent and 10 parts by weight of oxethylated nonylphenol as emulsifier.

e) Water-dispersible granules are obtained by mixing

| 75 parts by weight | of a compound of the formula (B1) and/or (B2) or of an active substance mixture of a herbicidal substance of the formula (A) and a safener of the formula B1 and/or B2, |
|---|---|
| 10 parts by weight | of calcium ligninsulfonate, |
| 5 parts by weight | of sodium lauryl sulfate, |
| 3 parts by weight | of polyvinyl alcohol and |
| 7 parts by weight | of kaolin, | grinding the mixture in a pinned-disc mill, and granulating the powder in a fluidized bed by spraying on water as granulation liquid.

f) Water-dispersible granules are also obtained by homogenizing and precomminuting

| | |
|---|---|
| 25 parts by weight | of a compound of the formula (B1) and/or (B2) or of an active substance mixture of a herbicidal active substance of the formula (A) and a safener of the formula (B1) and/or (B2), |
| 5 parts by weight | of sodium 2,2'-dinaphthyl-methane-6,6'-disulfonate, |
| 2 parts by weight | of sodium oleoylmethyltaurinate, |
| 1 parts by weight | of polyvinyl alcohol, |
| 17 parts by weight | calcium carbonate and |
| 50 parts by weight | water | in a colloid mill, subsequently grinding the mixture in a bead mill, and atomizing and drying the resulting suspension in a spray tower by means of a single-substance nozzle.

BIOLOGICAL EXAMPLES

Example 1

Wheat and barley (as crop plant) and silky bentgrass (as an example of a harmful plant) were grown in the greenhouse in plastic pots until they had reached the 3-leaf stage and then treated post-emergence with a mixture of the herbicide and the safener. The herbicide of the formula (A) and the compounds of the formula (B) were applied in the form of aqueous suspensions or emulsions at an application rate of 300 l of water/ha (converted). 4 weeks after treatment, the plants were scored visually for any type of damage caused by the herbicides applied, taking into account, in particular, the extent of sustained growth inhibition. They were assessed in percentages in comparison with untreated controls (see Table 1).

Even when massive overdoses of the herbicide are applied, severe damage in the crop plants is reduced markedly, and less damage is compensated for completely. The herbicidal activity of the compounds H1 and H2 was not adversely affected by the addition of the safeners according to the invention, as was shown with reference to silky bentgrass as an example.

Mixtures according to the invention of herbicides (A) and safeners (B) are therefore outstandingly suitable for the selective control of weeds in cereal crops.

TABLE 1

| Herbicide/Safener | Application rate [g of a.i./ha] | Post-emergence activity (in %) | | |
|---|---|---|---|---|
| | | Wheat* | Barley* | Silky bentgrass* (Apera spica-venti) |
| H1 | 50 | 75 | 80 | — |
| | 25 | 60 | 65 | 100 |
| | 12 | 40 | 50 | 98 |
| H1 + S1 | 50 + 25 | 20 | 45 | — |
| | 25 + 12 | 10 | 25 | 100 |
| | 12 + 6 | 0 | 15 | 98 |
| H1 + S2 | 50 + 25 | 15 | 50 | — |
| | 25 + 12 | 5 | 15 | 100 |
| | 12 + 6 | 0 | 5 | 99 |
| H1 + S3 | 50 + 25 | 30 | 50 | — |
| | 25 + 12 | 15 | 25 | 100 |
| | 12 + 6 | 5 | 10 | 98 |
| H1 + S4 | 50 + 25 | 25 | — | — |
| | 25 + 12 | 10 | — | 100 |
| | 12 + 6 | 5 | — | 99 |
| H1 + S5 | 50 + 25 | 15 | 40 | — |

TABLE 1-continued

| Herbicide/Safener | Application rate [g of a.i./ha] | Post-emergence activity (in %) | | |
|---|---|---|---|---|
| | | Wheat* | Barley* | Silky bentgrass* (Apera spica-venti) |
| | 25 + 12 | 10 | 20 | 100 |
| | 12 + 6 | 0 | 10 | 98 |
| H2 | 50 | 90 | 90 | — |
| | 25 | 65 | 65 | 100 |
| | 12 | 60 | 55 | 100 |
| H2 + S1 | 50 + 25 | 20 | 35 | — |
| | 25 + 12 | 0 | 20 | 100 |
| | 12 + 6 | 0 | 10 | 98 |
| H2 + S3 | 50 + 25 | 30 | 30 | — |
| | 25 + 12 | 10 | 10 | 98 |
| | 12 + 6 | 5 | 10 | 98 |
| H2 + S4 | 50 + 25 | 25 | 40 | — |
| | 25 + 12 | 10 | 10 | 98 |
| | 12 + 6 | 10 | 0 | 98 |
| H2 + S5 | 50 + 25 | 10 | 15 | — |
| | 25 + 12 | 10 | 10 | 99 |
| | 12 + 6 | 0 | 0 | 99 |
| H2 + S6 | 50 + 50 | 30 | 60 | — |
| | 25 + 25 | 20 | 55 | 95 |
| | 12 + 12 | 5 | 15 | 50 |
| H2 + S7 | 50 + 50 | 30 | 45 | — |
| | 25 + 25 | 20 | 35 | 95 |
| | 12 + 12 | 5 | 35 | 95 |

Abbreviations in Table 1:
* = wheat, barley and silky bentgrass in the 3-leaf stage
H1 = N-[(4-methoxy-6-methyl-1,3,5-triazine-2-yl)amino-carbonyl]-5-iodo-2-methoxycarbonyl-benzenesulfonamide
H2 = N-[(4-methoxy-6-methyl-1,3,5-triazine-2-yl)amino-carbonyl]-5-chloro-2-isopropoxycarbonyl-benzenesulfonamide
S1 = diethyl (5-chloro-8-quinolineoxy) malonate
S2 = 2-methylhexyl (5-chloro-8-quinolineoxy) acetate
S3 = ethyl 1-(2,4-dichlorophenyl)-5-(ethoxycarbonyl)-5-methyl-2-pyrazoline-3-carboxylate
S4 = ethyl 1-(2,4-dichlorophenyl)-5-trichloromethyl-(1H)-1,2,4-triazole-3-carboxylate
S5 = 1-methylethyl (5-chloro-8-quinolineoxy) malonate
S6 = 3,6-dichloro-2-methoxybenzoic acid (dicamba)
S7 = (R)-2-(4-chloro-2-methylphenoxy)propionic acid (mecoprop-P)
— = not tested.

EXAMPLE 2

Maize plants cvs. Felix and Dea were grown in the greenhouse in plastic pots until they had reached the 4-leaf stage and treated post-emergence with a mixture of herbicides (A) and safeners (B). The active substances were applied in the form of aqueous suspensions or emulsions at an application rate of 300 l of water/ha (converted). 4 weeks after treatment, the plants were scored visually for any type of damage caused by the herbicides applied, taking into account, in particular, the extent of sustained growth inhibition (Table 2).

They were assessed in percentages in comparison with untreated controls.

The results show that the compounds (B) are capable of effectively reducing herbicide damage suffered by the maize plants.

Even when massive overdoses of the herbicides are applied, severe damage in the crop plants is reduced markedly, and less damage is compensated for completely. Mixtures of herbicides (A) and safeners (B) are therefore outstandingly suitable for the selective control of weeds in maize.

TABLE 2

| Herbicide/Safener | Post-emergence effectiveness in % | | |
|---|---|---|---|
| | Application rate [g of a.i./ha] | Maize (Felix)* | Maize (Dea)* |
| H1 | 50 | 30 | 20 |
| | 25 | 20 | 10 |
| | 12 | 10 | 0 |
| H1 + S5 | 50 + 50 | 0 | 0 |
| | 25 + 25 | 0 | 0 |
| | 12 + 12 | 0 | 0 |

Abbreviations in Table 2:
* = 3-4-leaf stage
H1 = see Table 1
S5 = see Table 1

EXAMPLE 3

Rice was sown in plastic pots and grown in the greenhouse under optimum growth conditions. The plants were then treated with herbicides (A) and safeners (B) when they had reached the 4-leaf stage. 3 weeks after the treatment, the plants were scored for any type of herbicide damage, taking into account, in particular, the extent of sustained growth inhibition and thinning. The results show that the safeners effectively reduce herbicide damage suffered by rice.

Mixtures of herbicides (A) and safeners (B) are therefore suitable for the selective control of weeds in rice. The herbicidal activity of the herbicides employed against harmful plants was not adversely affected by adding the safeners according to the invention; at the application rates used, it corresponded to the comparison values as obtained when only the herbicides were used.

We claim:

1. A herbicide/safener combination, comprising

A) a herbicidal active substance from the group consisting of the substituted phenylsulfonylureas of the formula (A) and their salts,

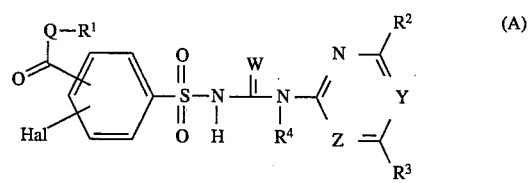

in which

Q and W are oxygen atoms,

Y and Z are nitrogen atoms, $R^1$ is hydrogen, $(C_1-C_6)$-alkyl,

Hal is chlorine, bromine or iodine, $R^2$ is methyl or methoxy, $R^3$ is methyl or methoxy and $R^4$ is hydrogen or methyl and B) at least one safener compound selected from the group consisting of the compounds of formula (B),

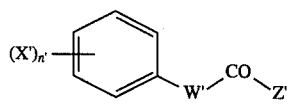

in which

W' is a group of the formula (W1)

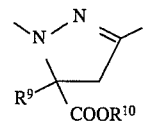

X' is hydrogen, halogen, methyl, ethyl, methoxy, ethoxy, halomethyl or haloethyl, Z' is $OR^7$ $R^7$ is hydrogen, $(C_1-C_8)$-alkyl, $(C_1-C_4)$-haloalkyl, $(C_1-C_4)$-hydroxyalkyl, $(C_1-C_7)$-cycloalkyl, $(C_1-C_8)$-alkoxy-$(C_1-C_4)$-alkyl, $R^9$ is hydrogen, $(C_1-C_8)$-alkyl, $(C_1-C_8)$-haloalkyl, $(C_3-C_7)$-cycloalkyl or phenyl, $R^{10}$ is hydrogen, $(C_1-C_8)$-alkyl, $(C_1-C_4)$-haloalkyl, $(C_1-C_8)$-alkoxy-$(C_1-C_4)$-alkyl, $(C_1-C_4)$-hydroxyalkyl or $(C_1-C_7)$-cycloalkyl, and n' is 1, 2, or 3.

2. A herbicide/safener combination as claimed in claim 1, comprising a herbicidal active substance from the group consisting of the substituted phenylsulfonylureas of the formula (a) and their salts in which $R^1$ is $(C_1-C_4)$-alkyl, Hal is chlorine or iodine $R^2$ is methyl or methoxy, $R^3$ is methyl or methoxy and $R^4$ is hydrogen.

3. A herbicide/safener combination as claimed in claim 2, comprising

B) at least one safener compound selected from the group consisting of the compounds of formula (B) in which W' is a group of the formula (W1)

X' is halogen

Z' is $OR^7$ $R^7$ is $(C_1-C_4)$-alkyl, $R^9$ is hydrogen, $(C_1-C_4)$-alkyl, $R^{10}$ is hydrogen, $(C_1-C_4)$-alkyl and n' is 1 or 2.

4. A herbicide/safener combination, as claimed in claim 3 comprising N-[4-methoxy-6-methyl-1,3,5-triazine-2-yl)aminocarbonyl]-5-iodo-2-methoxycarbonyl-benzenesulfonamide as herbicidal active substance.

5. A herbicide/safener combination as claimed in claim 3 comprising N-[4-methoxy-6-methyl-1,3,5-triazine-2-yl)aminocarbonyl]-5-chloro-2-isopropoxycarbonylbenzenesulfonamide as herbicidal active substance.

6. A herbicide/safener combination as claimed in claim 4 comprising ethyl 1-(2,4-dichlorophenyl)-5-(ethoxycarbonyl)-5-methyl-2-pyrazoline-3-carboxylate as safener compound.

7. A herbicide/safener combination as claimed in claim 5 comprising ethyl 1-(2,4-dichlorophenyl)-5-(ethoxycarbonyl)-5-methyl-2-pyrazoline-3-carboxylate as safener compound.

8. A herbicide/safener combination as claimed in claim 1 which is formulated in the form of a preparation (herbicidal composition) and comprises 0.1 to 95% by weight of active substances (A) and (B) and 1 to 99.9% by weight of conventional formulation auxiliaries.

9. A herbicide/safener combination as claimed in claim 1, which comprises the active substances (A) and (B) in a ratio by weight of 1:100 to 100:1.

10. A method of protecting crop plants against phytotoxic side-effects of herbicides (A), which comprises applying an effective amount of a type (B) safener to the plants, parts of the plants, seeds of the plants or the areas under cultivation either before, after, or simultaneously with, the herbicide (A), the combination of herbicide (A) and safener (B) being defined as claimed in claim 1.

11. The method as claimed in claim 10, wherein the crop plants are cereal plants, rice plants or maize plants.

12. The method as claimed in claim 10, wherein the compounds of the formula (A) or their salt are applied at an application rate of 0.001 to 10 kg of active ingredient/ha and a ratio by weight of safener:herbicide of 1:100 to 100:1.

13. A method of protecting crop plants against phytotoxic side-effects of herbicides (A), which comprises applying an effective amount of the safener compound ethyl 1-(2,4-dichlorophenyl)-5-(ethoxycarbonyl)-5-methyl-2-pyrazoline-3-carboxylate to the plants, parts of the plants or the area under cultivation either before, after or simultaneously with an effective amount of the herbicide N-[4-methoxy-6-methyl-1,3,5-triazine-2-yl)aminocarbonyl]-5-iodo-2-methoxycarbonyl-benzenesulfonamide.

14. A method of protecting crop plants against phytotoxic side-effects of herbicides (A), which comprises applying an effective amount of the safener compound ethyl 1-(2,4-dichlorophenyl)-5-(ethoxycarbonyl)-5-methyl-2-pyrazoline-3-carboxylate to the plants, parts of the plants or the area under cultivation either before, after or simultaneously with an effective amount of the herbicide N-[4-methoxy-6-methyl-1,3,5-triazine-2-yl)aminocarbonyl]-5-chloro-2-isopropoxycarbonylbenzenesulfonamide.

* * * * *